United States Patent [19]
Nishikawa et al.

[11] Patent Number: 5,481,946
[45] Date of Patent: Jan. 9, 1996

[54] PLUG-OPENING DEVICE FOR SEALED CONTAINER

[75] Inventors: Susumu Nishikawa, Shizuoka; Mariko Ikuma, Hamamatsu, both of Japan

[73] Assignee: System Stack, Co., Ltd., Hamana, Japan

[21] Appl. No.: 242,086

[22] Filed: May 12, 1994

[30] Foreign Application Priority Data

May 14, 1993 [JP] Japan .................................. 5-136665

[51] Int. Cl.⁶ ...................................................... B67B 7/00
[52] U.S. Cl. ...................................................... 81/3.2
[58] Field of Search .......................... 81/3.07, 3.2, 3.25, 81/3.31

[56] References Cited

U.S. PATENT DOCUMENTS

5,255,574  10/1993  Wuerschum ................................ 87/3.2
5,340,544  8/1994  Nishikawa et al. .................... 87/3.2 X Primary Examiner—James G. Smith
Attorney, Agent, or Firm—Armstrong, Westerman, Hattori, McLeland & Naughton

[57] ABSTRACT

A plug-opening device for a sealed type container, an opening of which is sealed with a sealing plug having a plug-opening tab, comprising a gripping mechanism for gripping the tab of the sealed container at a plug-opening position; and a plug-opening mechanism for moving the gripping mechanism passing through a position above the sealed container obliquely and upwardly on the side opposite to the position for the tab. The plug can be detached automatically from the opening reliably.

9 Claims, 9 Drawing Sheets

PLUG-OPENING DEVICE FOR SEALED CONTAINER

BACKGROUND OF THE INVENTION

1. Field of the Invention

The present Invention concerns a plug-opening device for a sealed container and, more in particular, it relates to a plug-opening device For opening a sealing type plug having a plug-opening tab.

2. Description of the Prior Art

Generally, in a vacuum blood sampling tube, an opening of which is sealed previously with a rubber plug having an aluminum foil, blood sampled from a human body is injected under sealed state by penetrating an injection needle through a rubber portion of the plug. Upon inspection, the plug of the vacuum sampling tube is opened for sampling a blood specimen.

By the way, since an utmost care has to be paid for the handling of tube plugs in order to prevent infectious disease, it has been demanded for the development of a plug-opening device capable of opening with no finger contact to a plug and various kinds of plug-opening devices have been proposed and put to practical use so far for an enforced type plug such as a rubber plug.

However, in a case of a sealing type plug employed for a vacuum blood sampling tube as described above, since the plug has to be opened by detaching the plug from the opening of the tube while gripping the, plug-opening tab, it is difficult to make the structure of the plug-opening device automatic and no effective plug-opening device regarding the plug of this sort has yet been developed at present.

OBJECT OF THE INVENTION

The present invention has been accomplished in view of the foregoing situations and it is an object of the present invention to provide a plug-opening device for a sealed container capable of reliably opening a sealing type plug by detaching the same from a sealed container with no finger touch.

SUMMARY OF THE INVENTION

The foregoing object of the present invention can be attained by a plug-opening device for a sealed type container an opening of which is sealed with a sealing plug having a plug-opening tab, comprising a gripping mechanism for gripping the tab of the sealed container at a plug-opening position; and a plug-opening mechanism for moving the gripping mechanism passing through a position above the sealed container obliquely and upwardly on the side opposite to the position for the tab.

In a preferred embodiment, the gripping mechanism comprises a chuck that opens and closes vertically for gripping a tab and a driving source for driving the chuck.

An electromagnetically driving source or a hydraulically driving source is preferably used for the driving source.

The gripping mechanism preferably comprises a support member secured to the plug-opening mechanism, a grip member that vertically penetrates the support member for seizing the tab between a chuck at the lower end and the lower surface of the support member and a spring normally biasing the grip member upwardly, in which the gripping mechanism is released by a driving mechanism for depressing the upper end of the grip member.

The plug-opening mechanism preferably has a rocking member of an inverted L-shaped configuration capable of rocking around a lower end as a fulcrum in a direction approaching to and away from the sealed container, and the driving mechanism preferably comprises a rocking rod secured at a lower end to a driving shaft passing through the fulcrum of the rocking member and driven to rock in the same direction as the rocking member, an interlock pin against which the rocking rod abuts upon rocking in the direction away from the sealed container and which transmits the rocking force of the rocking rod to the rocking member; and a rocking cam pivoted to the upper end of the rocking member, connected at an upper end by way of a link to the upper end of the rocking rod and depressing the upper end of the gripping member by the cam face.

In another preferred embodiment of the plug-opening device, the plug-opening mechanism comprises;

a guide cam hole that engages the gripping mechanism having a chuck driving portion and guides the gripping mechanism obliquely and upwardly from a position for the tab of the sealed container at a plug-opening position on the side opposite to the tab and a driving member for guiding the gripping mechanism reciprocally along the guide cam hole.

In a further preferred embodiment of the plug-opening device, the plug-opening mechanism comprises a hydraulically actuating cylinder having a stroke extensible from a position for the tab of the sealed container at a plug-opening position obliquely and upwardly on the side opposite to the tab, and a gripping mechanism having a chuck driving portion is attached to the top end of a cylinder rod of the cylinder.

The moving trace of the gripping mechanism preferably overlaps partially with the bending trace of the tab at a position above the sealed container.

In the plug-opening device for the sealed container according to the present invention, since the gripping mechanism that opens and closes vertically is adapted to move passing through a position above the sealed container obliquely and upwardly on the side opposite to the tab by the plug-opening mechanism, the tab is chucked in the vertical direction and pulled obliquely and upwardly in the direction opposite to that of the tab. Therefore, the plug is automatically detached from the opening as if it were peeled off by fingers and the plug is opened reliably.

Then, in the present invention, since the gripping mechanism comprises a chuck that opens and closes vertically for gripping the tab and a driving source for driving the chuck, it is possible to surely grip the tab even if the tab does not extend horizontally from the plug but is bent somewhat vertically. In this case, if an electromagnetically driving source or a hydraulically driving source is used for the driving source, the constitution of the device can be simplified.

Further, when the gripping mechanism comprises a support member, a grip member and a spring, and the gripping mechanism is adapted to open by the driving mechanism, it is no more necessary to move the gripping mechanism and the driving mechanism always integrally.

Further, when a rocking member is disposed to the plug-opening mechanism and the driving mechanism comprises a rocking rod, an interlock pin and a ,rocking cam, all the operations can be conducted by merely rocking the rocking rod.

Further, when the plug-opening mechanism comprises a hydraulically actuating cylinder in which a gripping mechanism is attached to the top end of a cylinder rod having an extensible stroke from a position for the tab obliquely and upwardly in the direction opposite to that of the tab, the gripping mechanism can be moved along a predetermined trace by merely extending and contracting the cylinder rod.

Furthermore, when the moving trace of the gripping mechanism and the bending trace of the tab are partially overlapped at a position above the sealed container, a tab bent upwardly from the plug can be gripped after turning it down in the horizontal direction by the gripping mechanism, by which more reliable gripping is possible.

BRIEF DESCRIPTION OF THE ACCOMPANYING DRAWINGS

The present invention will be described by way of its preferred embodiments in conjunction with the appended drawings, wherein.

DESCRIPTION OF THE PREFERRED EMBODIMENTS

Figure 1:
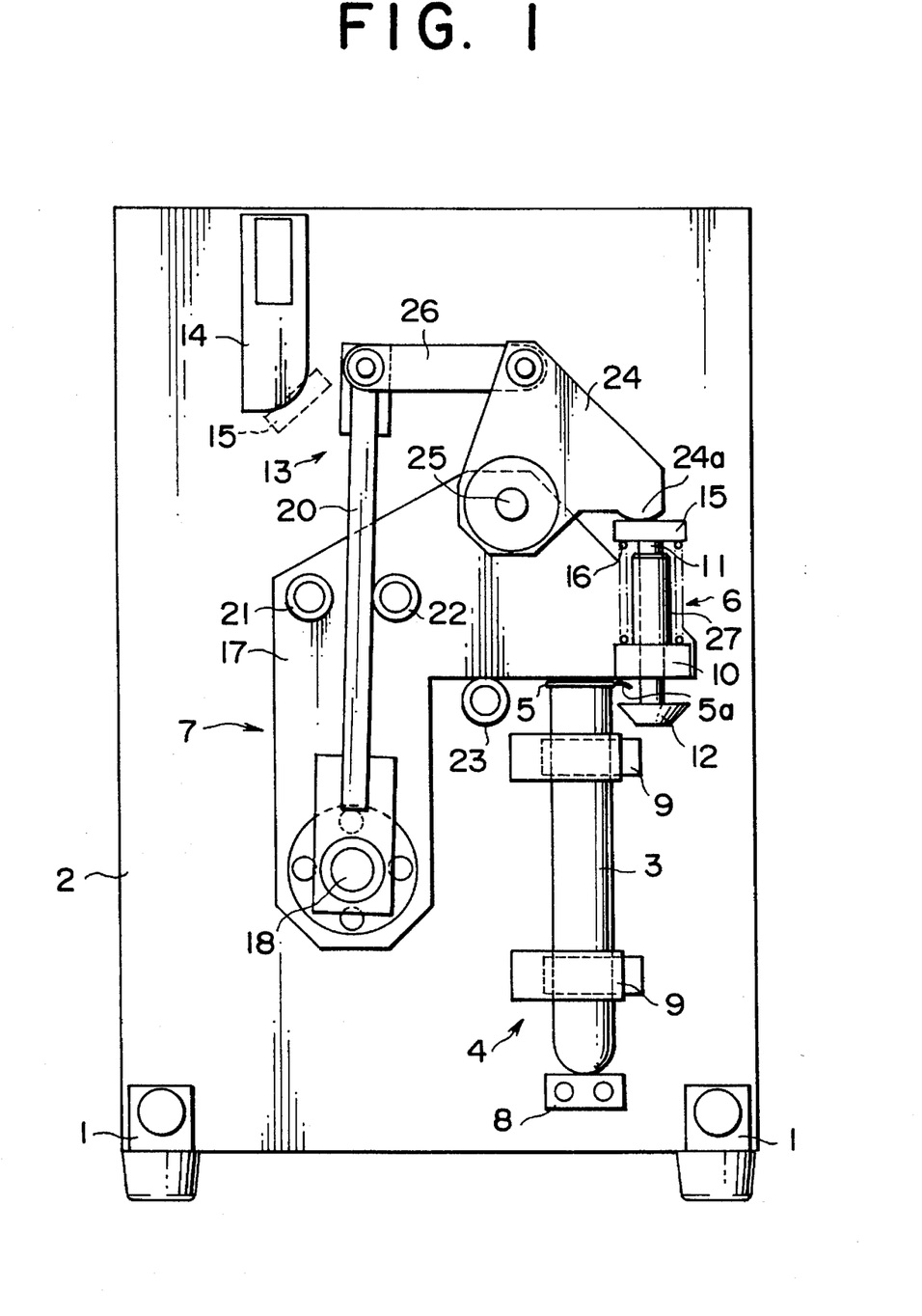
FIG. 1 is a front elevational view illustrating a plug-opening device for a sealed container in a preferred embodiment according to the present invention.
Figure 2:
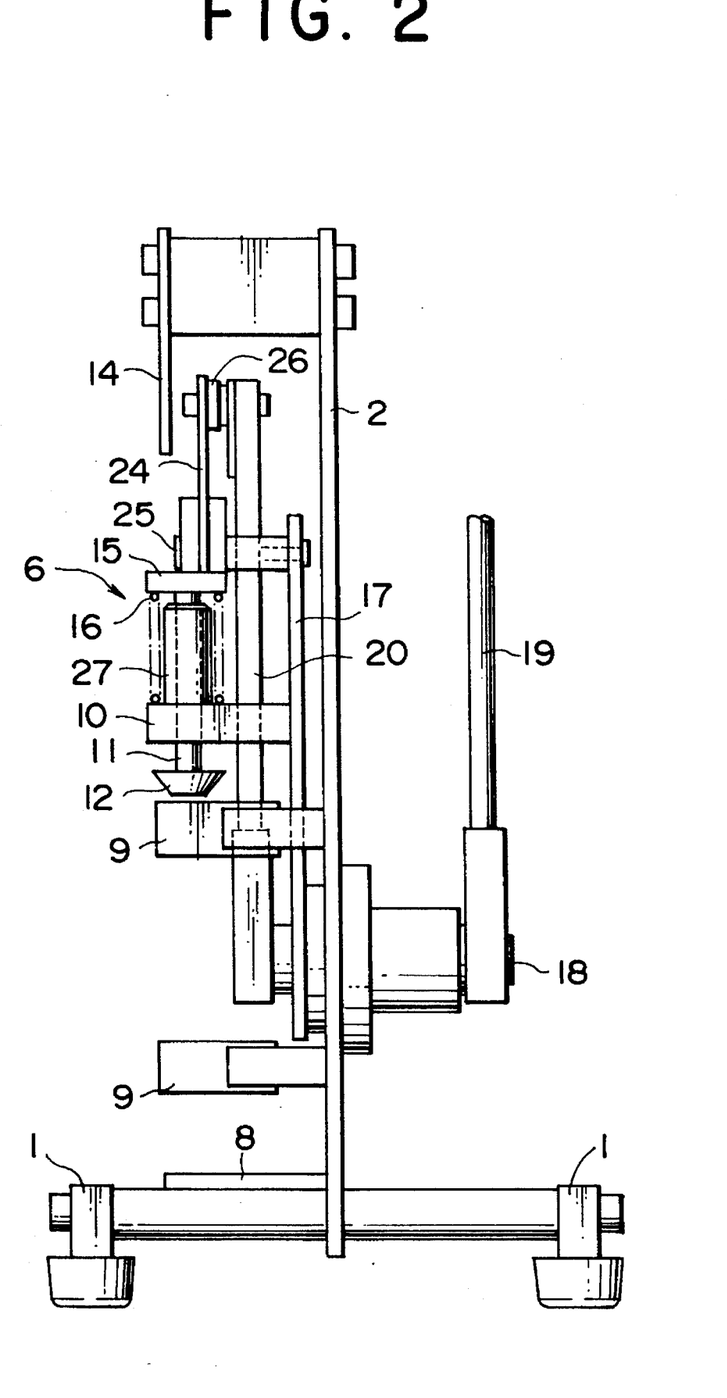
FIG. 2 is a right-hand side elevational view of the embodiment shown in FIG. 1.

FIGS. 1 and 2 show a plug-opening device for a sealed container in a first embodiment according to the present invention. The plug-opening device comprises a mounting substrate 2 held vertically on four setting legs 1. The mounting substrate 2 has, attached thereon, a securing mechanism 4 for a sealed container 3, a gripping mechanism 6 for gripping a tab 5a of a plug 5 that seals an opening of the sealed container 3 and a plug-opening mechanism 7 for moving the gripping mechanism 6 along a predetermined trace to be described later for opening the plug 5, respectively.

As shown in FIGS. 1 and 2, the securing mechanism 4 comprises a receiving stand 8 that supports the lower end of the sealed container 3 for positioning the sealed container 3 vertically, and two holders 9 for holding the sealed container 3 at an intermediate vertical portion. A leaf spring is incorporated to each of the holders 9, so that the sealed container 3 is snap-fitted to each of the holders 9 and held stably by enforcing the sealed container 3 laterally from the right in FIG. 1.

As shown in FIGS. 1 and 2, the gripping mechanism 6 comprises a support member 10 fixed to the plug-opening mechanism 7 to be detailed later and a grip member 11 that penetrates the support member 10 vertically. A chuck 12 of an inverted frustconical shape is secured to the lower end of the grip member 11 for seizing the tab 5a between it and the lower surface of the support member 10. An upper end flange 15 secured to the upper end of the grip member 11 and is adapted to be depressed by a driving mechanism 13 and a driving member 14 to be described later. A spring 16 is interposed between the upper flange 15 of the grip member 11 and the support member 11 for normally biasing the grip member 11 upwardly. The gripping mechanism 6 is usually put under a chuck-closed state by the resilient force of the spring 16.

Then, as shown in FIGS. 1 and 2, the plug-opening mechanism 7 has a rocking member 17 of an inverted L-shaped configuration capable of rocking around the lower end as a fulcrum in the directing approaching to and away from the sealed container 3. The driving mechanism 13 is disposed on the front side of the rocking member 17 and the driving member 14 is secured to the mounting substrate 2 at a position above the rocking member 17.

As shown in FIGS. 1 and 2, the driving mechanism 13 has a driving shaft 18 that passes through the fulcrum of the rocking member 17 and pivotally supporting the rocking member 17. A handle 19 is secured to the end of the driving shaft 18 at the back of the mounting substrate 2 for driving the driving shaft 18, and a lower end of a rocking rod 20 is secured to the end of the driving shaft 18 on the front side of the mounting substrate 2. The rocking rod 20 is adapted to rock in the same direction as the rocking member 17 by manipulating the driving handle 19.

As shown in FIG. 1, an interlock pin 21 that transmits the rocking force of the rocking rod 20 to the rocking member 17 and a stopper pin 22 that restricts the rocking range of the rocking rod 20 to the side of the sealed container 3 are attached, respectively, on both lateral sides of the rocking rod 20 of the rocking member 17. Each of the pins 21 and 22 has an eccentric circular cam structure so that a timing abutting against the rocking rod 20 can be adjusted finely.

As shown in FIG. 1, the range for the rocking movement of the rocking member 17 toward the sealed container 3 is restricted by a stopper pin 23 attached to the substrate 2. The stopper pin 23, like the stopper pin 22, has an eccentric circular cam structure so that the timing abutting against the rocking member 17 can be adjusted finely.

As shown in FIGS. 1 and 2, a rocking cam 24 generally of a trigonal shape is pivoted at a lower end by way of a fulcrum pin 25. The upper end of the rocking cam 24 is connected by way of a link 26 to the upper end of the rocking rod 20. A cam face 24a of the cam 24 is brought into contact with the upper surface of the upper end flange 15 of the grip member 11 of the gripping mechanism 6. By the rocking movement of the rocking cam 24 caused by the rocking rod 20, the grip member 11 is caused to slide downwardly against the resilient force of the spring 16 such that the chuck 12 of the gripping mechanism 6 is put under a chuck-open state relative to the support member 10.

As shown in FIGS. 1 and 2, the driving member 14 is formed as a plate cam, against which the upper end flange 15 of the grip member 11 of the gripping mechanism 6 abuts when the rocking member 17 rocks counterclockwise in FIG. 1 and is depressed against the spring 16 to put the gripping mechanism 6 under the chuck-open state, so that the plug 5 seized between the chuck 12 and the support member 10 is released from gripping and allowed to drop downwardly.

The range for the rocking movement of the rocking member 17 in the counterclockwise direction is restricted by the abutment of the upper end flange 15 against a guide cylinder 27 that is erected on the upper surface of the support member 10 and guides the vertical movement of the grip member 11.

Descriptions will then be made to the operation of this embodiment.

Figure 3:
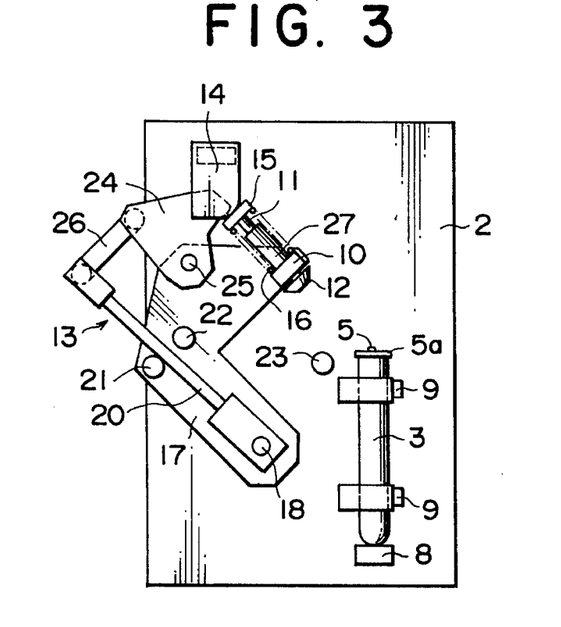
FIG. 3 is an explanatory view illustrating a state of the plug-opening device in a first stage of a plug-opening operation.

Upon opening a plug, the sealed container 3 is at first mounted and secured to the securing mechanism 4 as shown in FIG. 3. In this instance, the tab 5a of the plug 5 is situated to the right in the drawing as shown in FIG. 3.

Figure 4:
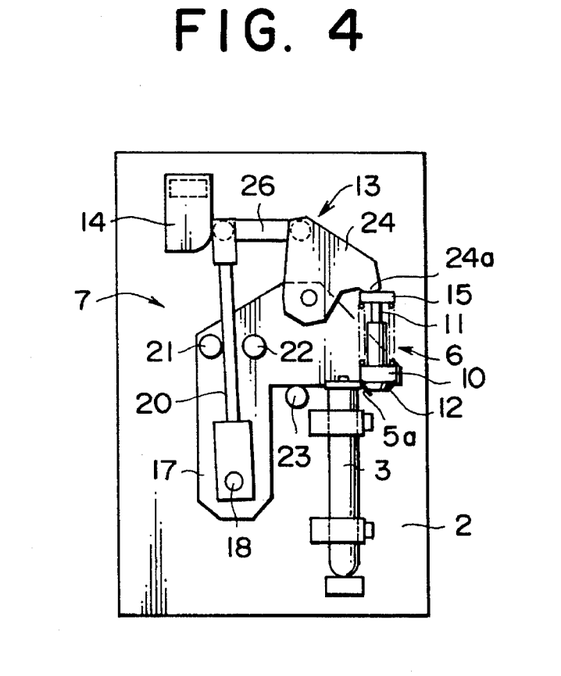
FIG. 4 is an explanatory view illustrating a state of the plug-opening device in a second stage of a plug-opening operation.

Then, when the driving handle 19 (refer to FIG. 2) is manipulated to rotate the driving shaft 18 clockwise in FIG. 3, the rocking rod 20 and the rocking member 17 rock integrally clockwise in the drawing and then, as shown in FIG. 4, the rocking member 17 abuts against the stopper pin 23 to be restricted from further rocking.

Figure 5:
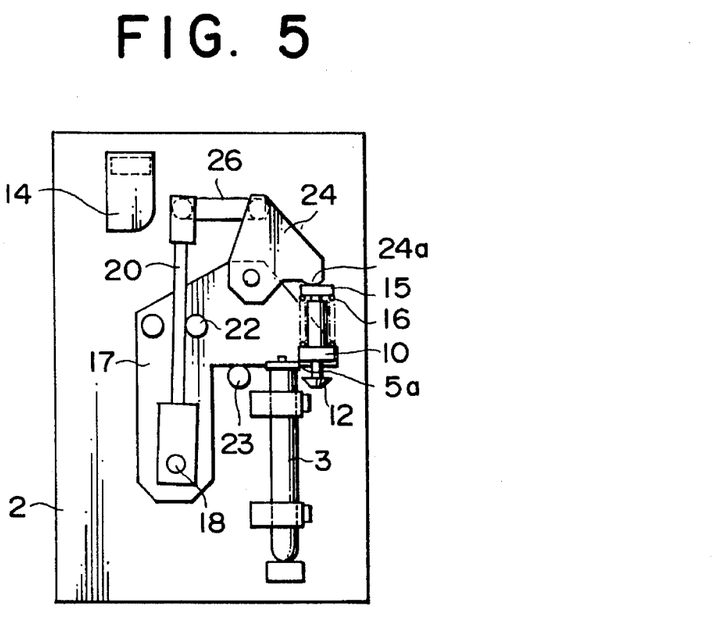
FIG. 5 is an explanatory view illustrating a state of the plug-opening device in a third stage of a plug-opening operation.

When the driving shaft 18 is caused to rotate further clockwise in this state, only the rocking rod 20 rocks to a position abutting against the stopper pin 22 as shown in FIG. 5. Then, the upper end flange 15 of the grip member 11 is depressed by the cam face 24a of the rocking cam 24, by which the chuck 12 lowers to a chuck-open state.

Then, when the driving handle 19 is manipulated in an opposite direction to rotate the driving shaft 18 counter-clockwise in FIG. 5, only the rocking rod 20 at first rocks to a position abutting against the interlock pin 21, so that the depressing force to the upper end flange 15 by the rocking cam 24 is removed. Accordingly, the grip member 11 moves upwardly by the resilient force of the spring 16 to seize the tab 5a between the lower surface of the support member 10 and the chuck 12.

Figure 6:
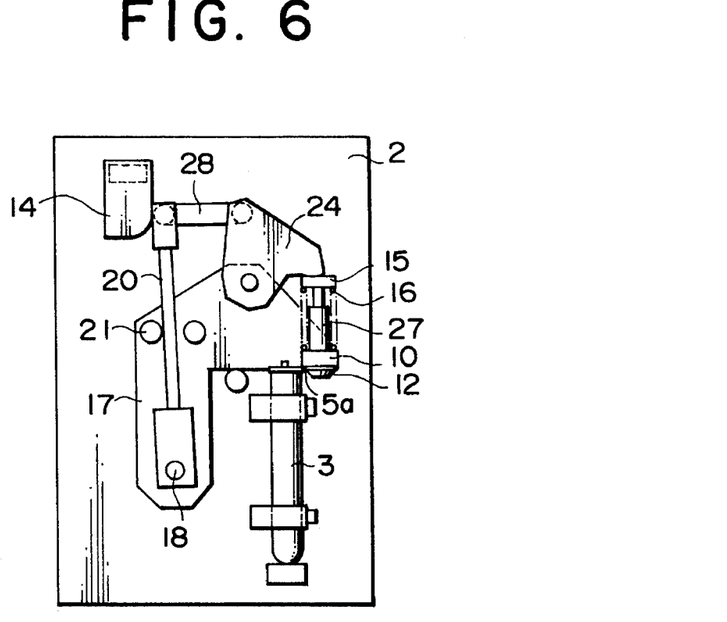
FIG. 6 is an explanatory view illustrating a state of the plug-opening device in a fourth stage of a plug-opening operation.
Figure 7:
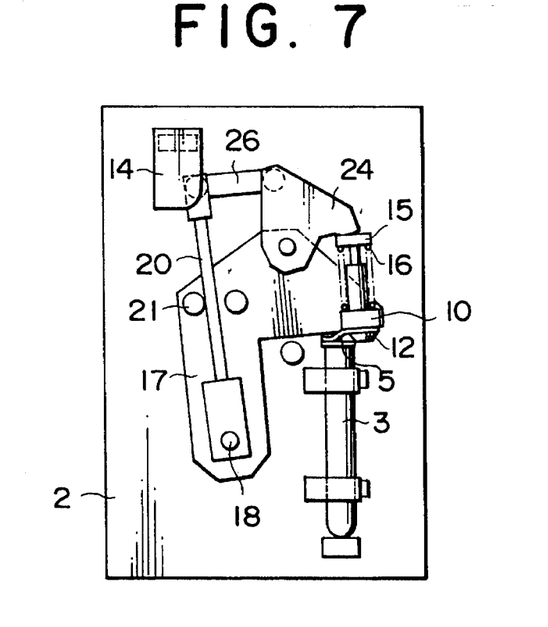
FIG. 7 is an explanatory view illustrating a state of the plug-opening device in a fifth stage of a plug-opening operation.
Figure 8:
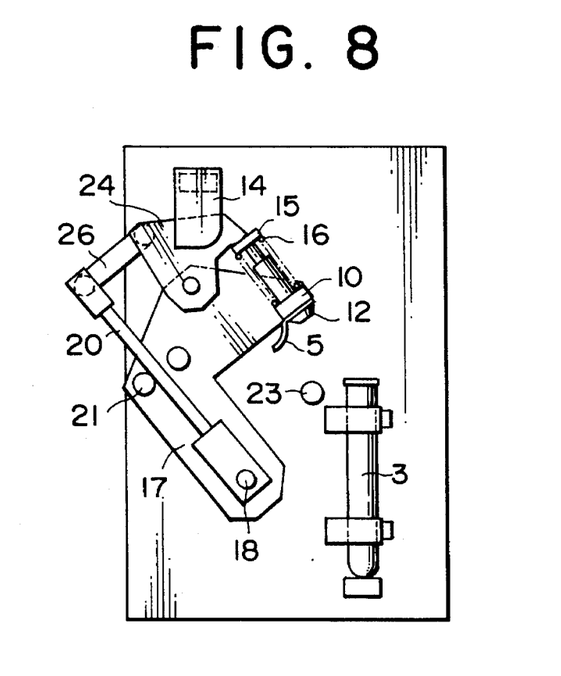
FIG. 8 is an explanatory view illustrating a state of the plug-opening device in a sixth stage of a plug-opening operation.

When the driving handle 19 is further manipulated from this state, to rotate the driving shaft 18 counter-clockwise in FIG. 6, the rocking force of the rocking rod 20 is transmitted by way of the interlock pin 21 to the rocking member 17, by which the rocking rod 20 and the rocking member 17 rock integrally counterclockwise as shown in FIGS. 7 and 8, and the gripping mechanism 6 moves obliquely and upwardly on the side opposite to the tab 5a passing through a position above the sealed container 3. Therefore, the plug 5 is detached as if it were peeled by fingers and the sealed container 3 is opened.

Figure 9:
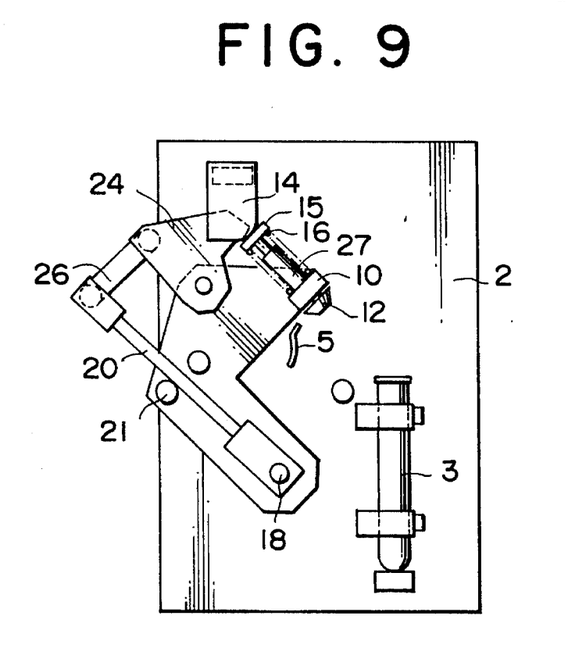
FIG. 9 is an explanatory view illustrating a state of the plug-opening device in a seventh stage of a plug-opening operation.

Then, when the driving shaft 18 is further rotated counterclockwise from this state, the upper end flange 15 of the gripping mechanism 6 abuts against the driving member 14 as shown in FIG. 9 and is depressed by the rotation of the driving shall 18. This depresses the grip member 11 against the resilient force of the spring 16 into a chuck-open state, and the plug 5 with its tab 5a seized between the support member 10 and the chuck 12 is caused to drop.

Subsequently, the device returns to the state shown in FIG. 3 and the foregoing operations are repeated to successively open the sealed containers 3.

Figure 10:
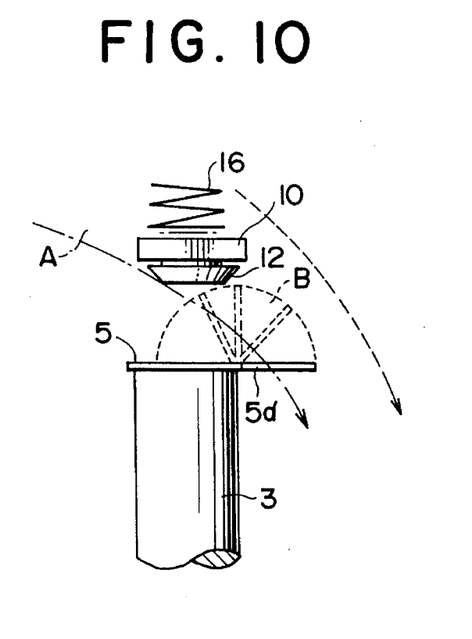
FIG. 10 is an explanatory view illustrating a state in which a moving trace of a gripping mechanism overlaps a bending trace of a tab.

By the way, when the gripping mechanism 6 moves from the state shown in FIG. 3 to a state shown in FIG. 4, a moving trace A of the gripping mechanism 6 and a bending trace B of the tab 5a partially overlap to each other at a position above the sealed container 3 as shown in FIG. 10. Therefore, even if the tab 5a is bent and raises upwardly from the plug 5, the tab 5a is turned down into a horizontal state by the chuck 12 moving from the state shown in FIG. 3 to the state shown in FIG. 4, so that the tab 5a can be held surely. In addition, since the chuck has an inverted frust-conical shape, the tab 5a is not turned down excessively, so that it is free from a disadvantage that the tab 5a bends downwardly and can not be held.

Then, the plug 5 can surely be peeled and removed by merely rotating the driving handle 19 and there is no worry that obstacles should intrude into the sealed container 3 upon opening the plug 5.

Although descriptions have been made in the first embodiment to a case of driving the driving shaft 18 by the driving handle 19, it may be automated by driving, for example, with a brake motor.

Further, although not illustrated, automation can also be attained, for example, by connecting a motor-rotated arm with the driving handle 19 by means of a crank, so that the driving handle 19 is caused to rock for a predetermined angle by one rotation of the motor.

Figure 11:
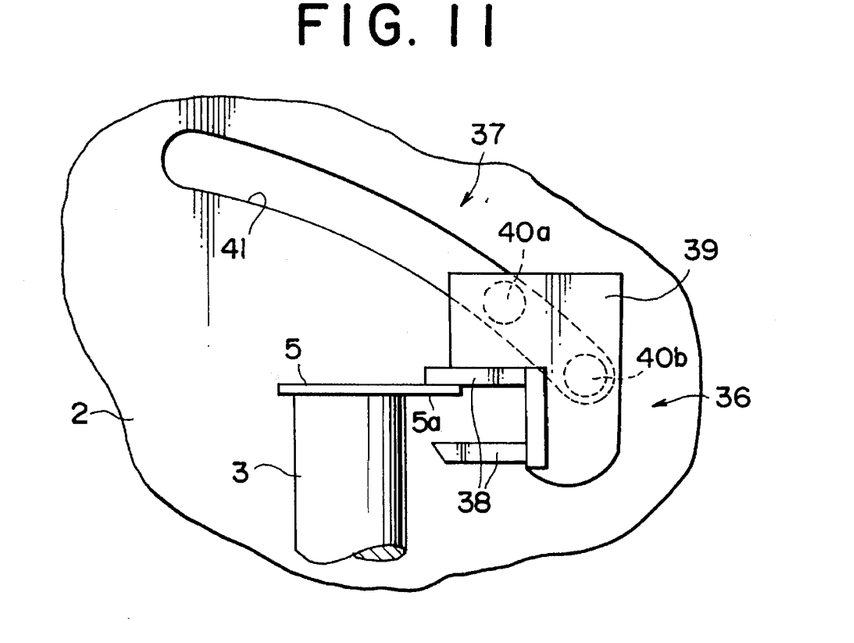
FIG. 11 is a fragmentary view for the constitution of a second embodiment according to the present invention.
Figure 12:
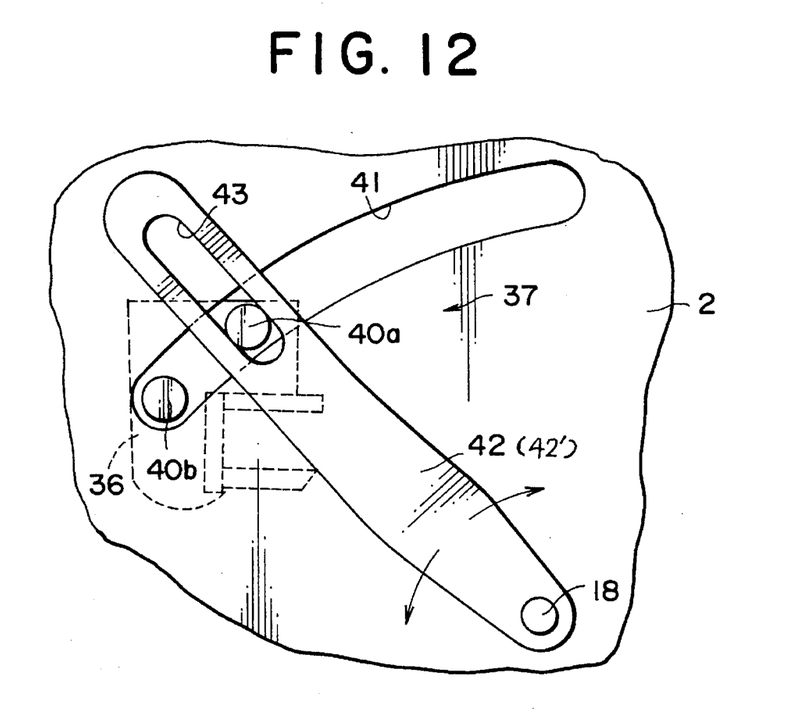
FIG. 12 is a rear elevational view for the embodiment shown in FIG. 11.

FIGS. 11 and 12 show a second embodiment of the present invention, in which a gripping mechanism 36 and a plug-opening mechanism 37 are used instead of the gripping mechanism 6 and the plug-opening mechanism 7 in the first embodiment described above.

Namely, the gripping mechanism 36 comprises, as shown in FIG. 11, a chuck 38 which opens and closes vertically for gripping a tab 5a and a driving source 39 for driving the chuck 38 by a fluid pressure or electromagnetic force.

Further, the plug-opening mechanism 37 comprises, as shown in FIGS. 11 and 12, two guide pins 40a and 40b protruding at the back of the driving source 39, a long guide cam hole 41 formed to a mounting substrate 2 and a driving member 42 for moving the gripping mechanism 36 along the guide cam hole 41. Then, in the embodiment shown in FIGS. 11 and 12, a rocking arm 42' is used as the driving member 42 in the embodiment shown in FIGS. 11 and 12.

Namely, in the plug-opening mechanism 37 shown in FIGS. 11, 12, the two guide pins 40a, 40b protruding at the back of the gripping mechanism 36 are fitted into and engaged with the guide cam hole 41, and the guide pins 40a, 40b are engaged to an engaging hole 43 of the rocking arm 42' supported pivotally by the driving shaft 18.

Thus, it is so adapted that rocking movement of the rocking arm 42' causes the gripping mechanism 36 that engages therewith by way of the guide pins 40a, 40b, to move along the guide cam hole 41 while being kept at a constant attitude.

Other constitutions and the operations are the same as those in the first embodiment described previously.

Descriptions have been made for the embodiments shown in FIGS. 11 and 12 to a case of using the rocking arm 42' as the driving member 42 thereby moving the gripping mechanism 36 along the guide cam hole 41. Alternatively, a hydraulic pressure cylinder may be used instead of the rocking arm 42, and the gripping mechanism 36 may be reciprocated along the guide cam hole 41 by the stroke of the cylinder rod.

Then, in this embodiment, since the chuck 38 is driven by a hydraulically driving or electromagnetically driving source 39, constitution of the gripping mechanism 36 and the plug-opening mechanism 37 can be simplified.

Figure 13:
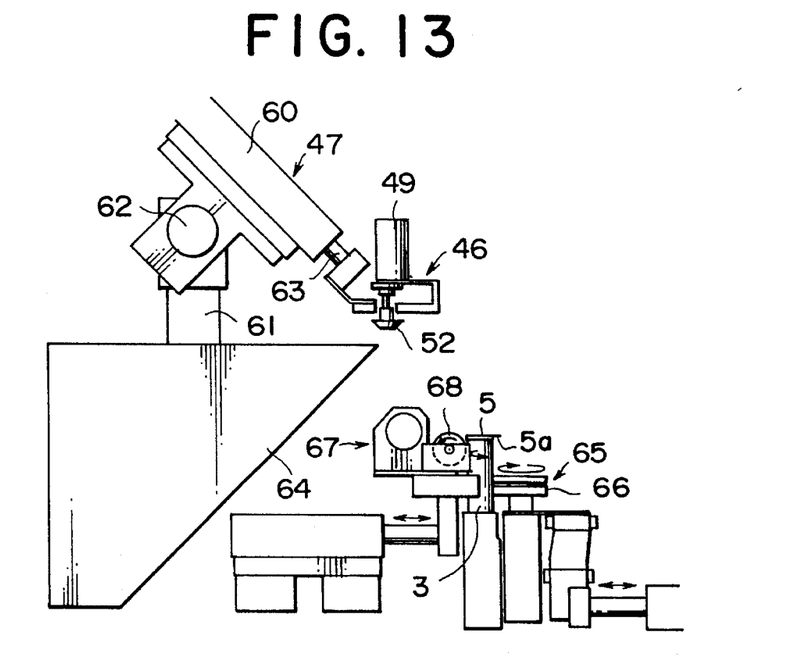
FIG. 13 is a fragmentary view for the constitution of a third embodiment according to the present invention.

FIG. 13 shows a third embodiment of the present invention. In this embodiment, a gripping mechanism 46 has a constitution of opening and closing a chuck 52 by a hydraulically or electromagnetically driving source 49 and a hydraulically actuating cylinder 60 Is provided as a plug-opening mechanism 47 for reciprocating the gripping mechanism 46 from a position for the tab 5a of the container 3 obliquely and upwardly on the side opposite to the tab position.

The cylinder 60 for the plug-opening mechanism 47 is mounted by way of a bearing portion 62 capable of freely adjusting an angle to a frame 61 situated obliquely upwardly of the sealed container 3 at a plug-opening position, and the gripping mechanism 46 is attached to the top end of a cylinder rod 63.

Then, the gripping mechanism 46 at the top end of the cylinder rod 63 is disposed at such an angle and an extensible stroke as capable of linearly moving from a position for the tab of the container 3 at a plug-opening position obliquely and upwardly on the side opposite to the tab position.

Figure 14:
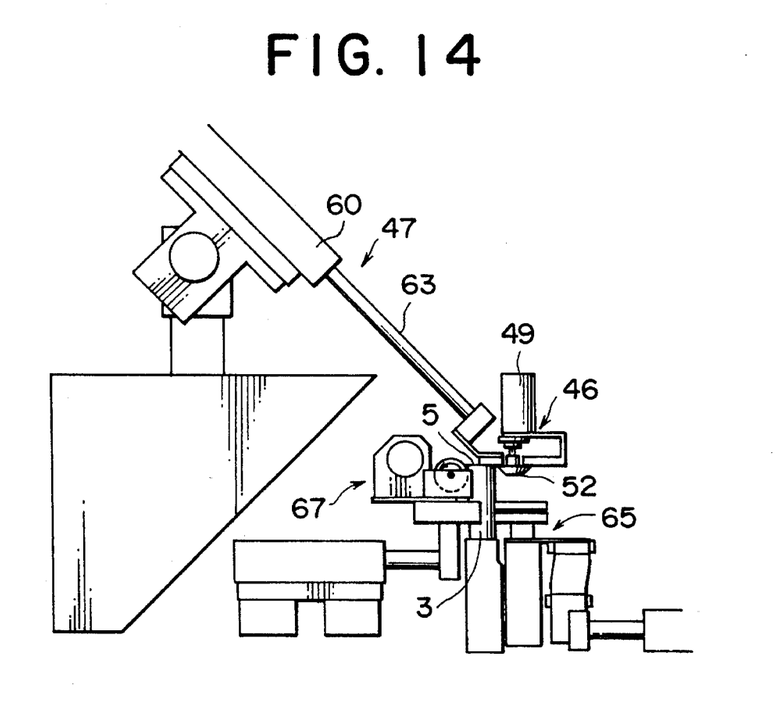
FIG. 14 is an explanatory view for a plug-opening operation in the embodiment shown in FIG. 13.

Thus, as shown In FIG. 1.4, after extending the cylinder 63 to move the gripping mechanism 46 at the top end to the tab position of the container 3, the chuck 52 is closed to grip the tab 5a.

Figure 15:
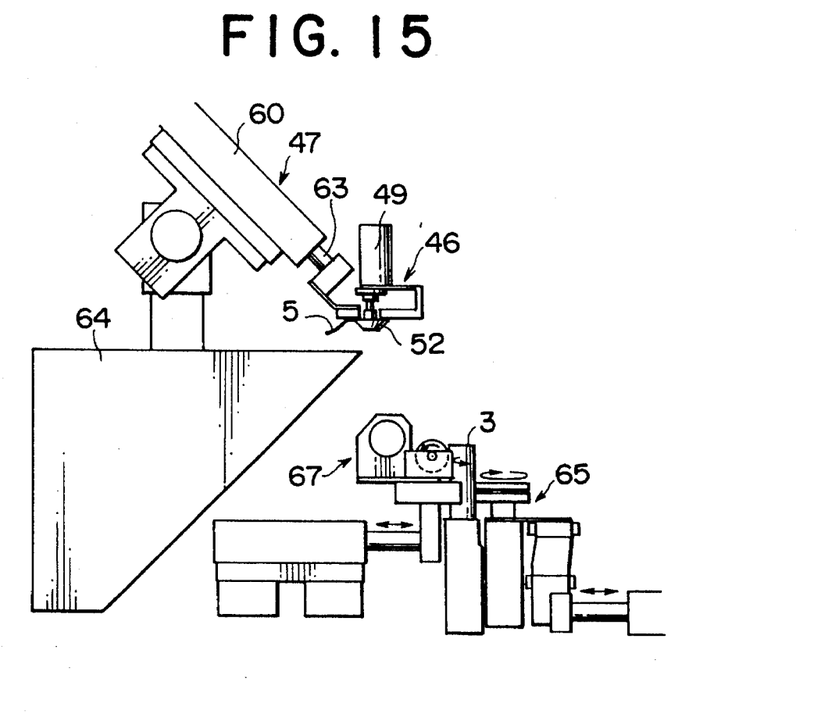
FIG. 15 is an explanatory view for a plug-opening operation in the embodiment shown in FIG. 13.

Then, as shown in FIG. 15, the gripping mechanism 46 is moved through a portion above the top end of the container 3 obliquely and upwardly on the opposite side by a contracting stroke of the cylinder rod 63, by which the tab 5a is detached from the container 3 and transferred together with the gripping mechanism 46 obliquely and upwardly.

When the chuck 52 of the gripping mechanism 46 is opened at that position, the tab 5a is detached from the gripping mechanism 46 and then discharged to a hopper 64.

In FIGS. 13 and 14, reference numeral 65 denotes a tab position amending device that detects the tab 5a of the plug 5 while rotating the container 3 around its axis by a horizontally rotational roller 66 and adjusts the tab 5a to a predetermined direction and a reference numeral 67 denotes an attitude amending device that turns up the tab 5a of the plug 5 at a plug-opening position in the horizontal direction by a vertically rotational brush 68. The tab 5a of the sealed container 3 placed at random is always directed to the chuckling position of the gripping mechanism 46 by the attitude amending device 67 and the tab position amending device 65.

When the gripping mechanism 46 lowers to a position for the tab of the container 3, the tab 5a may some time be bent downwardly by the top end of the chuck 52, making it impossible to grip the tab 5a.

Figure 16:
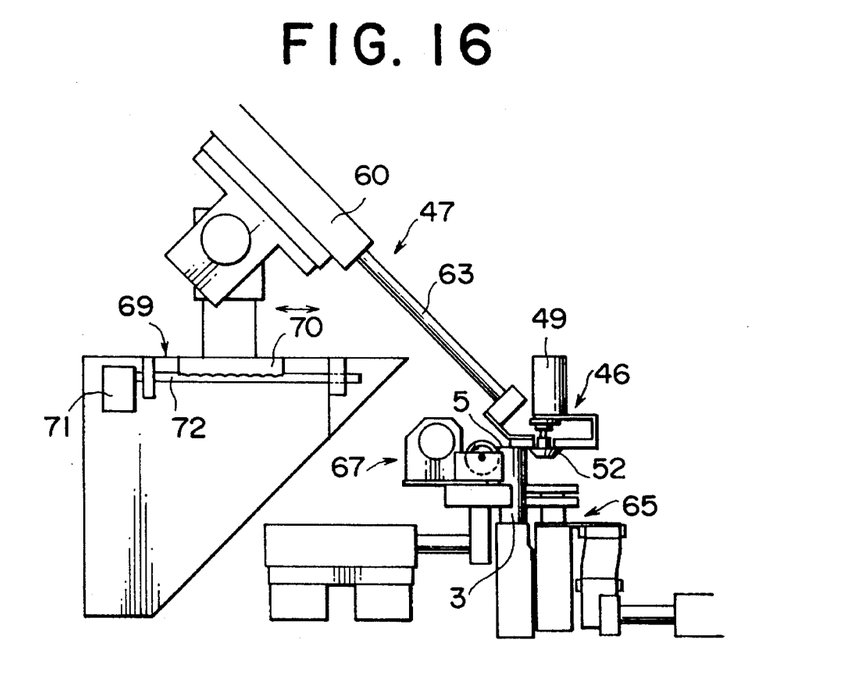
FIG. 16 is an explanatory view of a plug-opening operation in the embodiment shown in FIG. 13 including a slidable gripping mechanism on the hopper.

In order to solve this problem, it is preferred to provide a sliding mechanism 69 for moving the gripping mechanism 46 horizontally at a position for the tab of the container 3.

As shown in FIG. 16, the slide mechanism 69 may have a structure in which a base 70 of a plug-opening mechanism 47 is to a hopper 64 slidably in the horizontal direction, and a base 70 itself of the plug-opening mechanism 47 is moved horizontally, for example, by a driving device (not illustrated) having a feed screw 72 rotated forwardly and backwardly by a servomotor 71. Alternatively, it may have a structure in which the gripping mechanism 46 is slidably engaged to a horizontal frame at the top end of the cylinder rod 63 and moved horizontally by a driving device (not illustrated).

In the illustrated embodiments, the top end at each of the chucks 12, 38, 52 for seizing the tab 5a is made into an acute angle, so that area of contact with the tab 5a and the chuck is made smaller when the latter lowers to thereby facilitate return of the tab 5a by its rebounding force to the upper side on each of the chucks 12, 38, 52.

Although descriptions have been made to the previous embodiments in a case of opening the sealed container 3 one by one, a plurality of sealed containers can be opened simultaneously or in an interlocking manner by using a plurality sets of the plug-opening units. For instance, a plurality of sealed containers 3 may be arranged at a predetermined interval to the left of FIG. 2 and a plurality of rocking members 17 may be disposed corresponding thereto, so that a plurality or sealed container 3 can be opened simultaneously by using a single driving shaft 18.

As has been described above according to the present invention, since the gripping mechanism for gripping the tab of the plug is adapted to move passing through a position above the sealed container obliquely and upwardly on the side opposite to the tab by the plug-opening mechanism, the plug can be detached from the opening as if it were peeled off by fingers thereby enabling to open the plug surely.

Further, in the present invention, since the gripping mechanism comprises a chuck that opens and closes vertically for gripping the tab and a driving source for driving the chuck, the tab can be gripped surely even if it does not extend horizontally but is bent somewhat vertically. In this case, the constitution of the device can be simplified by using an electromagnetically or hydraulically driving source as the driving source.

Further, if the gripping mechanism comprises a support member, a grip member and a spring, in, which the gripping mechanism is opened by a driving mechanism, there is no more necessary to always move the gripping mechanism and the driving mechanism integrally .

Further, when a rocking member is disposed to the plug-opening mechanism and the driving mechanism comprises a rocking rod, an interlock pin and a rocking cam, all the operations can be conducted by merely rocking the rocking rod.

Furthermore, when a cylinder is used for the plug-opening mechanism that moves the gripping mechanism, the device may be made compact and the operation can be made smooth.

Furthermore, when a moving trace of the gripping mechanism and a bending trace of the tab are partially overlapped at a position above the seated container, the tab bent upwardly from the plug sealed gripped after turning it down in the horizontal direction by the gripping mechanism and can be gripped more reliably.

What is claimed is:

1. A plug-opening device for a sealed container having an upwardly facing opening which is sealed with a sealing type plug having a plug-opening tab extending laterally therefrom, comprising;

a gripping mechanism for gripping upper and lower sides of the tab of the sealed container at a plug-opening position at a first side of the sealed container; and a plug-opening mechanism for moving said gripping mechanism from the plug-opening position through a position above said sealed container obliquely across said opening and upwardly to a second side of the sealed container opposite to said first side to a position for placing the tab.

2. A device as defined in claim 1, wherein the gripping mechanism comprises a chuck that opens and closes vertically for gripping the tab and a driving source for driving said chuck.

3. A device as defined in claim 2, wherein an electromagnetically driving source or a hydraulically driving source is used as the driving source.

4. A device as claimed in claim 1, wherein the gripping mechanism comprises:

a support member secured to the plug-opening mechanism, a grip member that vertically penetrates said support member for seizing a tab between a chuck at a lower end and a lower surface of said support member and a spring always biasing said grip member upwardly, in which the gripping mechanism is released by a driving mechanism for depressing an upper end of said grip member.

5. A device as defined in claim 4, wherein the plug-opening mechanism has a rocking member of an inverted L-shaped configuration capable of rocking around a lower end at a fulcrum in a direction approaching to and away from the sealed container, and the driving mechanism comprises a rocking rod secured at a lower end to a driving shaft passing through the fulcrum of said rocking member and driveable to rock in the same direction as the rocking member, an interlock pin against which said rocking rod abuts upon rocking in a direction away from the sealed container and which transmits a rocking force of said rocking rod to said rocking member; and a rocking cam pivoted to an upper end of said rocking member, a link connected at an upper end of the rocking cam to an upper end of said rocking rod and said rocking cam having a cam face arranged to depress the upper end of said grip member by the cam face.

6. A device as defined in any one of claims 1 to 3, wherein the plug-opening mechanism comprises:

a guide cam hole that extends obliquely and upwardly from the plug-opening position to the position for placing the tab;

said gripping mechanism having a guide member which is guided along said guide cam hole; and a driving member for guiding said gripping mechanism reciprocally along said guide cam hole.

7. A device as defined in any one of claims 1 to 3, wherein the plug-opening mechanism comprises a hydraulically actuating cylinder having a stroke extensible from the position for placing the tab to the plug-opening position obliquely across said opening and upwardly, and said gripping mechanism having a chuck driving portion attached to a top end of a cylinder rod of said cylinder.

8. A device as defined in claim 7, which further comprises a slide mechanism for moving the gripping mechanism in a horizontal direction.

9. A device as defined in any one of claims 1 to 5, wherein a moving trace of the gripping mechanism and a bending trace of the tab partially overlap each other at a position above the sealed container.

* * * * *